US00PP14968P2

(12) United States Plant Patent
Sakazaki

(10) Patent No.: US PP14,968 P2
(45) Date of Patent: Jun. 29, 2004

(54) CALIBRACHOA PLANT NAMED 'USCALI11'

(50) Latin Name: *Calibrachoa sp.*
Varietal Denomination: USCALI11

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 10/638,686

(22) Filed: Aug. 11, 2003

(51) Int. Cl.[7] ..... A10H 5/00
(52) U.S. Cl. ..... Plt./263
(58) Field of Search ..... Plt./263

*Primary Examiner*—Anne Marie Grunberg
*Assistant Examiner*—June Hwu
(74) *Attorney, Agent, or Firm*—C. A. Whealy

(57) ABSTRACT

A distinct cultivar of Calibrachoa plant named 'USCALI11', characterized by its semi-upright plant habit; freely branching habit; freely flowering habit; large light red purple-colored flowers; good weather tolerance; and resistance to Thielaviopsis.

1 Drawing Sheet

Botanical classification/cultivar designation: Calibrachoa sp. cultivar USCALI11

BACKGROUND OF THE INVENTION

The present Invention relates to a new and distinct cultivar of Calibrachoa plant, botanically known as Calibrachoa sp., and hereinfter referred to by the cultivar name 'USCALI11'.

The new Calibrachoa is a product of a planned breeding program conducted by the Inventor in Hikone, Shiga, Japan. The objective of the program is to create new heat-tolerant and disease-resistant Calibrachoa cultivars with semi-upright plant habit and attractive flower colors.

The new Calibrachoa originated from a cross made by the Inventor On May 10, 1998 of a proprietary seedling selection of Calibrachoa identified as code number CJ19-3, not patented, as the female, or seed, parent with a proprietary seedling selection of Calibrachoa identified as code number CJ18-8, not patented, as the male, or pollen, parent. The new Calibrachoa was selected by the Inventor on Jun. 15, 1999 in a controlled environment in Gensingen, Germany.

Asexual reproduction of the new cultivar by terminal cuttings taken in a controlled environment in Gensingen, Germany since Jun. 25, 1999, has shown that the unique features of this new Calibrachoa are stable and reproduced true to type in successive generations.

SUMMARY OF THE INVENTION

Plants of the cultivar USCALI11 have not been observed under all possible environmental conditions. The phenotype may vary somewhat with variations in environment such as temperature, light intensity, daylength, water status and fertility level without, however, any variance in genotype.

The following traits have been repeatedly observed and are determined to be the unique characteristics of 'USCALI11'. These characteristics in combination distinguish 'USCALI11' as a new and distinct cultivar of Calibrachoa:

1. Semi-upright plant habit.
2. Freely branching habit.
3. Freely flowering habit.
4. Large light red purple-colored flowers.

5. Good weather tolerance; tolerant to rain and low and high temperatures.
6. Resistant to Thielaviopsis.

Plants of the new Calibrachoa differ primarily from plants of the parent selections in plant habit as plants of the female selection are more upright than plants of the new Calibrachoa and plants of the male parent are more trailing than plants of the new Calibrachoa.

Plants of the new Calibrachoa can be compared to plants of the cultivar Colorburst Rose, disclosed in U.S. Plant Pat. No. 12,147. In side-by-side comparisons conducted in Gensingen, Germany, plants of the new Calibrachoa had a more upright plant habit and differed in flower coloration compared to plants of the cultivar Colorburst Rose.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa.

The photograph at the top of the sheet comprises a side perspective view of three typical plants of 'USCALI11' grown in a hanging basket container.

The photograph at the bottom of the sheet is a close-up view of typical flowers and leaves of 'USCALI11'.

DETAILED BOTANICAL DESCRIPTION

In the following description, color references are made to The Royal Horticultural Society Colour Chart, 1995 Edition, except where general terms of ordinary dictionary significance are used. Plants grown in 15-cm containers with three plants per container were used for the aforementioned photographs and following description. Plants were about four weeks from planting rooted cuttings. Plants were grown under conditions which closely approximate commercial production conditions during the spring in Bonsall, Calif. in an outdoor nursery. During the production period, day temperatures ranged from 18 to 35° C. and night temperatures ranged from 7 to 18° C.

Botanical classification: Calibrachoa sp. cultivar USCALI11.

Parentage:

*Female, or seed, parent.*—Proprietary seedling selection of Calibrachoa sp. identified as code number CJ19-3, not patented.

*Male, or pollen, parent.*—Proprietary seedling selection of Calibrachoa sp. identified as code number CJ18-8, not patented.

Propagation:

*Type cutting.*—Terminal vegetative cuttings.

*Time to initiate and develop roots.*—Summer: About 21 days at 20° C. Winter: About 28 days at 20° C.

*Root description.*—Fine, freely-branching; whitish in color.

Plant description:

*Form.*—Annual flowering plant; initially upright to semi-upright, eventually somewhat cascading; uniformly mounded appearance.

*Usage.*—Appropriate for hanging baskets, window boxes and patio containers.

*Plant height* (*from soil level to top of plant plane*).—About 15 cm.

*Plant diameter* (*area of spread*), *single plant.*—About 26 cm.

*Growth rate.*—Moderate to rapid; vigorous.

*Branching habit.*—Freely branching, about six lateral branches per plant, pinching is typically not required.

*Lateral branch description.*—Length: About 25 cm. Diameter: About 2 mm. Internode length: About 2.5 cm. Texture: Pubescent. Color: 144A.

*Foliage description.*—Arrangement: Alternate until flowering, then opposite; simple. Length: About 3.2 cm. Width: About 1.2 cm. Shape: Elliptic. Apex: Broadly acute to rounded. Base: Attenuate. Margin: Entire. Texture, upper and lower surfaces: Slightly pubescent. Venation pattern: Pinnate; arcuate. Color: Developing foliage, upper and lower surfaces: 144A. Fully expanded foliage, upper and lower surfaces: 147A. Venation, upper surface: 145A. Venation, lower surface: 147B. Petiole: Length: About 7 mm. Diameter: About 2 mm. Color: 145B.

Flower description:

*Flower type and habit.*—Flowers face upright or outward; single, axillary; salverform. Flowers persistent. Freely flowering habit, about 8 to 10 open flowers and about 12 to 14 flower buds per lateral stem. Flowers not fragrant.

*Natural flowering season.*—April to October in Southern California; flowering continuous.

*Time to flower.*—Early flowering; plants begin flowering about four weeks after planting.

*Flower longevity on the plant.*—About five to ten days.

*Flower size.*—Diameter: About 2.9 cm. Tube length: About 2.8 cm.

*Flower buds* (*before showing color*).—Length: About 2 cm. Diameter: About 4 mm. Shape: Roughly oblong. Color: 84B.

*Corolla.*—Arrangement/appearance: Single whorl or five petals, fused into flared trumpet. Petal length from throat: About 1.1 cm. Petal width: About 1.4 cm. Petal shape: Roughly spatulate. Petal apex: Obtuse. Petal margin: Entire. Petal texture, upper and lower surfaces: Smooth, glabrous; velvety. Color: Petal, when opening, upper surface: 74A. Petal, when opening, lower surface: 70B. petal, opened flower, upper surface: 74B, venation and towards throat, 74A; flower color becoming closer to 72C with subsequent development. Petal, opened flower, lower surface: 70B to 70C. Flower throat (inside): 12A. Flower tube (outside): 10B.

*Sepals.*—Arrangement/appearance: Single whorl of five sepals, fused at base; star-shaped. Length: About 1.4 cm. Width: About 3 mm. Shape: Narrowly elliptic. Apex: Broadly acute. Margin: Entire. Texture, upper and lower surfaces: Pubescence. Color, upper and lower surfaces: 146A.

*Peduncles.*—Length: About 2 cm. Width: About 1 mm. Strength: Strong. Angle: Erect to about 30 to 45° from vertical. Texture: Pubescence. Color: 144A.

*Reproductive organs.*—Stamens: Quantity: Five per flower. Anther shape: Oval. Anther length: Less than 1 mm. Anther color: 11A. Pollen amount: Scarce. Pollen color: 11A. Pistils: Quantity: One per flower. Pistil length: About 1.1 cm. Stigma shape: Anvil-shaped. Stigma color: 144B. Style length: About 8 mm. Style color: 144C. Ovary color: 145B.

*Seed/fruit.*—Seed and fruit production has not been observed.

Disease/pest resistance: Plants of the new Calibrachoa have been noted to be resistant to Thielaviopsis. Plants of the new Calibrachoa have not been noted to be resistant to other pathogens and pests common to Calibrachoas.

Weather/temperature tolerance: Plants of the new Calibrachoa are tolerant to rain and wind and have been observed to tolerate temperatures from −4 to 38° C.

It is claimed:

1. A new and distinct cultivar of Calibrachoa plant named 'USCALI11', as illustrated and described.

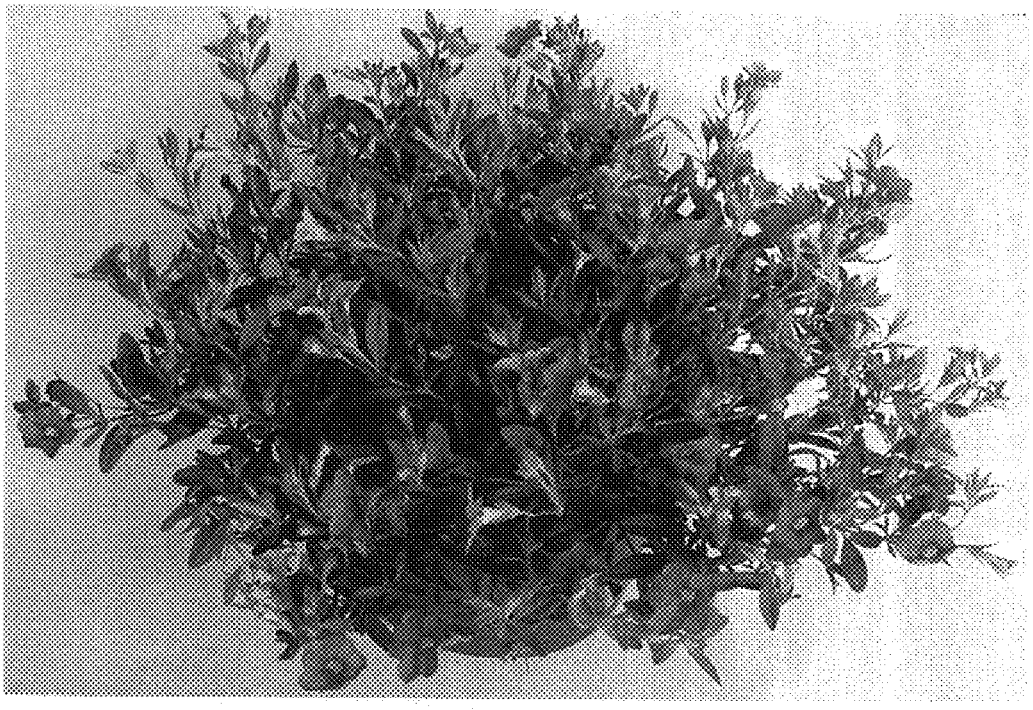
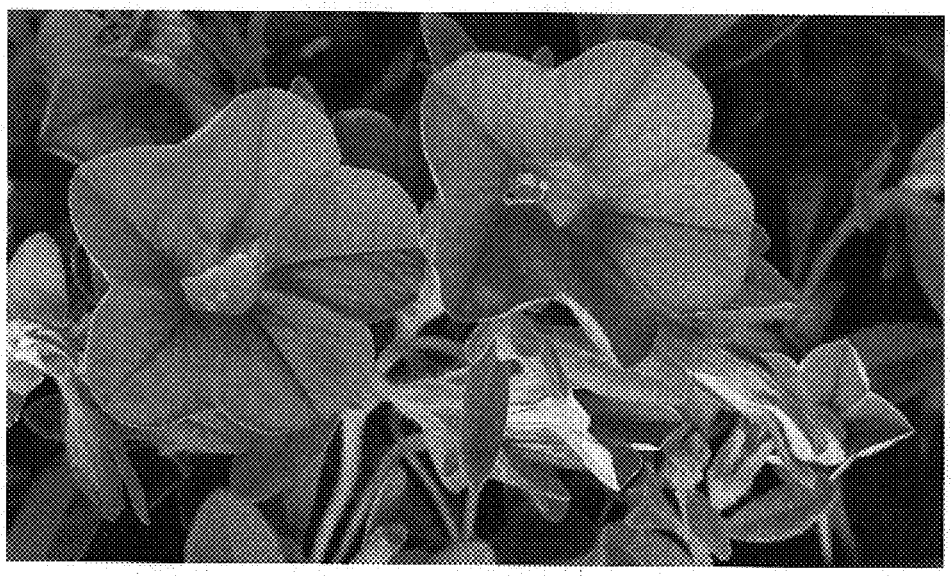

* * * * *